US010816621B2

(12) United States Patent
Dumoulin et al.

(10) Patent No.: US 10,816,621 B2
(45) Date of Patent: *Oct. 27, 2020

(54) MAGNETIC RESONANCE SIGNAL DETECTOR GRID ASSEMBLIES FOR MAGNETIC RESONANCE IMAGING

(71) Applicant: CHILDREN'S HOSPITAL MEDICAL CENTER, Cincinnati, OH (US)

(72) Inventors: Charles Lucian Dumoulin, Cincinnati, OH (US); Wolfgang Manfred Loew, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 144 days.

This patent is subject to a terminal disclaimer.

(21) Appl. No.: 16/014,143

(22) Filed: Jun. 21, 2018

(65) Prior Publication Data

US 2018/0299519 A1 Oct. 18, 2018

Related U.S. Application Data

(63) Continuation-in-part of application No. 14/814,002, filed on Jul. 30, 2015, now Pat. No. 10,031,195.
(Continued)

(51) Int. Cl.
*G01R 33/341* (2006.01)
*G01R 33/36* (2006.01)
(Continued)

(52) U.S. Cl.
CPC ............ *G01R 33/341* (2013.01); *A61B 5/055* (2013.01); *G01R 33/3415* (2013.01);
(Continued)

(58) Field of Classification Search
CPC ....................... G01R 33/3621; G01R 33/3628; G01R 33/04; G01R 33/34007; G01R 33/3415;
(Continued)

(56) References Cited

U.S. PATENT DOCUMENTS 4,859,950 A   8/1989   Keren
5,284,144 A   2/1994   DeLannoy et al.
(Continued)

FOREIGN PATENT DOCUMENTS

WO   WO 2008/115426 A1   9/2008

*Primary Examiner* — Vinh P Nguyen
(74) *Attorney, Agent, or Firm* — BakerHostetler

(57) ABSTRACT

A magnetic resonance (MR) signal detector grid assembly adapted for detection of signals in a magnetic resonance imaging apparatus is disclosed. The MR signal detector grid assembly may include a non-resonant grid of a plurality of wire elements and a plurality of detector elements. At least one end of a selected wire element may be electrically attached to an end of at least one other selected wire element. At least one of the detector elements may be configured to detect an MR signal induced on a wire element in the non-resonant grid. The plurality of wire elements may be substantially in the same plane, and the plane may be warped into an arbitrary three-dimensional surface. The three-dimensional surface may have a shape that is cylindrical, partially cylindrical, and/or saddle-shaped. The plurality of wire elements may form a rectilinear grid, a hexagonal grid, a triangular grid, and/or a pseudo-random grid.

17 Claims, 11 Drawing Sheets

Related U.S. Application Data

(60) Provisional application No. 62/031,119, filed on Jul. 30, 2014.

(51) Int. Cl.

| | | |
|---|---|---|
| A61B 5/055 | (2006.01) | |
| H01F 27/28 | (2006.01) | |
| H03H 7/38 | (2006.01) | |
| H01F 19/04 | (2006.01) | |
| G01R 33/3415 | (2006.01) | |

(52) U.S. Cl.
CPC ..... G01R 33/3628 (2013.01); G01R 33/3642 (2013.01); H01F 19/04 (2013.01); H01F 27/2823 (2013.01); H03H 7/38 (2013.01)

(58) Field of Classification Search
CPC ............ G01R 33/3607; G01R 33/3685; G01R 33/3642; G01R 33/341; A61N 1/403; A61N 1/37211; A61N 1/3727; A61B 5/117; A61B 17/66; A61B 17/68; A61B 17/7062; A61B 2017/00398; A61B 2017/00411; A61B 2017/00539; A61B 2017/0256; A61B 5/0006; A61B 5/055; H01F 27/2823; H01F 19/04; H03H 7/38
See application file for complete search history.

(56) References Cited

U.S. PATENT DOCUMENTS

| | | | |
|---|---|---|---|
| 5,430,378 A | 7/1995 | Jones | |
| 5,477,146 A | 12/1995 | Jones | |
| 5,905,378 A | 5/1999 | Giaquinto et al. | |
| 6,084,411 A | 7/2000 | Giaquinto et al. | |
| 6,249,121 B1 | 6/2001 | Boskamp et al. | |
| 6,501,274 B1 | 12/2002 | Ledden | |
| 6,608,480 B1 | 8/2003 | Weyers | |
| 6,750,652 B2 | 6/2004 | Weyers et al. | |
| 7,012,429 B1 | 3/2006 | Ledden | |
| 7,088,104 B2 | 8/2006 | Bottomley | |
| 7,141,980 B2 | 11/2006 | Belt et al. | |
| 7,253,622 B2 | 8/2007 | Saylor et al. | |
| 7,282,915 B2 | 10/2007 | Giaquinto et al. | |
| 7,345,485 B2 | 3/2008 | Jevtic et al. | |
| 7,378,851 B1 | 5/2008 | De Rooij et al. | |
| 7,443,163 B2 | 10/2008 | Warntjes et al. | |
| 7,508,212 B2 | 3/2009 | Fain et al. | |
| 7,602,187 B2 | 10/2009 | Luedeke et al. | |
| 7,652,476 B2 | 1/2010 | De Rooij et al. | |
| 7,714,581 B2 | 5/2010 | Erickson et al. | |
| 7,733,092 B2 | 6/2010 | Otake et al. | |
| 7,795,870 B2 | 9/2010 | Sodickson et al. | |
| 7,970,452 B2 | 6/2011 | Piron et al. | |
| 7,973,614 B2 | 7/2011 | Taracila et al. | |
| 8,179,137 B2 | 5/2012 | Feng et al. | |
| 8,193,810 B2 | 6/2012 | Otake et al. | |
| 8,193,812 B2 | 6/2012 | Pinkerton et al. | |
| 8,212,630 B2 | 7/2012 | Endo | |
| 8,369,930 B2 | 2/2013 | Jenkins et al. | |
| 8,421,461 B2 | 4/2013 | Cork et al. | |
| 8,547,102 B2 | 10/2013 | Nozaki | |
| 8,922,213 B2 | 12/2014 | Nozaki | |
| 9,274,084 B2 | 3/2016 | Goodwill et al. | |
| 9,279,863 B2 | 3/2016 | Tsukamoto | |
| 9,459,331 B2 | 10/2016 | Otake et al. | |
| 9,520,636 B2 | 12/2016 | Ferrand et al. | |
| 9,535,142 B2 | 1/2017 | Leussler et al. | |
| 9,599,685 B2 | 3/2017 | Habara et al. | |
| 9,625,551 B2 | 4/2017 | Ozen et al. | |
| 10,031,195 B2 * | 7/2018 | Dumoulin | G01R 33/3415 |
| 2004/0075435 A1 | 4/2004 | Weyers et al. | |
| 2005/0253582 A1 | 11/2005 | Giaquinto et al. | |
| 2008/0136414 A1 | 6/2008 | De Rooij et al. | |
| 2008/0306377 A1 | 12/2008 | Piron et al. | |
| 2010/0256480 A1 | 10/2010 | Bottomley et al. | |
| 2010/0312096 A1 | 12/2010 | Guttman et al. | |
| 2011/0025326 A1 * | 2/2011 | Zens | G01R 33/302 324/307 |
| 2011/0267062 A1 | 11/2011 | Otake et al. | |
| 2012/0262177 A1 | 10/2012 | Eiermann et al. | |
| 2013/0093425 A1 | 4/2013 | Chu et al. | |
| 2013/0285760 A1 | 10/2013 | Liu et al. | |
| 2015/0355297 A1 | 12/2015 | Menon et al. | |

* cited by examiner

MAGNETIC RESONANCE SIGNAL DETECTOR GRID ASSEMBLIES FOR MAGNETIC RESONANCE IMAGING

CROSS-REFERENCE TO RELATED APPLICATIONS

The present application is a Continuation in Part of U.S. application Ser. No. 14/814,002, filed Jul. 30, 2015, which claims priority to and the benefit of U.S. Provisional Application Ser. No. 62/031,119, filed Jul. 30, 2014, the disclosures of which are incorporated herein by reference.

BACKGROUND

In magnetic resonance imaging (MRI), surface coils are placed close to the desired object to be imaged to maximize the signal-to-noise ratio (SNR). High performance surface coils are typically combined to form phased arrays comprised of overlapped single loop coils. These phased arrays offer the SNR of small surface coils over a field-of-view (FOV) of a larger surface coil. Phased arrays are used to achieve high resolution imaging of different parts of the body. In addition to offering a SNR advantage, multiple independent receive elements can enable accelerated imaging techniques.

Traditional phased array designs are limited because they have to be customized to each body part. Customization criteria include shape and impedance matching. Further, a large number of components are required for this traditional approach.

SUMMARY

The present disclosure describes a magnetic resonance (MR) detector that may replace conventional MR imaging coil arrays. The present disclosure describes an example coil design approach that may reduce the number of components for MR imaging devices and may eliminate the need of tissue matching. This new approach implements a non-resonant grid in which MR-induced currents are allowed to flow unconstrained over the grid (unlike conventional phased array coils in which current is constrained to flow within each loop). Current in each element of the grid may be detected with inductively-coupled pickup loops, which may be attached to independent receiver channels of the MR imaging system. In one example, individual integrated balun pickup coils may be inductively coupled to each grid element. Other connection arrangements, however, may be employed if desired.

In a first aspect, the present disclosure discloses an example coil array assembly adapted for detection of signals in a magnetic resonance imaging (MRI) apparatus. The coil array assembly may include a non-resonant grid of transformer elements and pickup coils. Each pickup coil may be inductively coupled to a corresponding transformer element in the non-resonant grid. Each pickup coil may be configured to detect an MR signal induced on a corresponding wire element in the non-resonant grid of wire elements.

In a second aspect, the present disclosure discloses a radio frequency (RF) coil assembly for use in a magnetic resonance imaging (MRI) system. The RF coil assembly may include coil array elements adapted to connect to a corresponding plurality of signal lines in the MRI system. Each of the coil array elements may include a non-resonant grid of transformer elements and pickup coils. Each pickup coil may be inductively coupled to a corresponding transformer element in the non-resonant grid. Each pickup coil may include a loop coil body of conductor material and a matching circuit electrically coupled to the loop coil body and adapted to be electrically coupled to one of the plurality of signal lines in the MRI system. The loop coil body structure may include an integrated balun.

In a third aspect, the present disclosure discloses a magnetic resonance (MR) signal detector grid assembly adapted for the detection of signals in a magnetic resonance imaging (MRI) apparatus. The MR signal detector grid assembly may comprise a non-resonant grid of a plurality of wire elements and a plurality of detector elements. At least one end of a selected wire element may be electrically attached to an end of at least one other selected wire element. At least one of the detector elements may be configured to detect an MR signal induced on a wire element in the non-resonant grid. The plurality of wire elements may be substantially in the same plane, and the plane may be warped into an arbitrary three-dimensional surface. The three-dimensional surface may have a shape that is cylindrical, partially cylindrical, and/or saddle-shaped. The plurality of wire elements may form a rectilinear grid, a hexagonal grid, a triangular grid, and/or a pseudo-random grid.

BRIEF DESCRIPTION OF THE DRAWINGS

The foregoing and other features of the present disclosure will become more fully apparent from the following description, taken in conjunction with the accompanying drawings. Understanding that these drawings depict only several embodiments in accordance with the disclosure and are therefore not to be considered limiting of its scope, the disclosure will be described with additional specificity and detail through use of the accompanying drawings.

In the drawings.

DETAILED DESCRIPTION

The present disclosure describes a magnetic resonance (MR) detector that may replace conventional MR imaging coil arrays. The present disclosure describes an example coil design approach that may reduce the number of components for MR imaging devices and may eliminate the need of tissue matching. This new approach implements a non-resonant grid in which MR-induced currents are allowed to flow unconstrained over the grid (unlike conventional phased array coils in which current is constrained to flow within each loop). Current in each element of the grid may be detected with inductively-coupled pickup loops, which may be attached to independent receiver channels of the MR imaging system. In one example, individual integrated balun pickup coils may be inductively coupled to each grid element. Each pickup coil may be configured to detect an MR signal induced on a corresponding wire element in the non-resonant grid of wire elements. Other connection arrangements, however, may be employed if desired. A pickup coil may also be referred to herein as a "detector element."

MR imaging of internal body tissues may be used for numerous medical procedures, including diagnosis and surgery. In general terms, MR imaging starts by placing a subject in a relatively uniform, static magnetic field. The static magnetic field causes hydrogen nuclei spins to align and precess about the general direction of the magnetic field. Radio frequency (RF) magnetic field pulses are then superimposed on the static magnetic field to cause some of the aligned spins to alternate between a temporary high-energy nonaligned state and the aligned state, thereby inducing an RF response signal, called the MR echo or MR response signal. It is known that different tissues in the subject produce different MR response signals, and this property can be used to create contrast in an MR image. An RF receiver detects the duration, strength, and source location of the MR response signals, and such data are then processed to generate tomographic or three-dimensional images.

Figure 1:
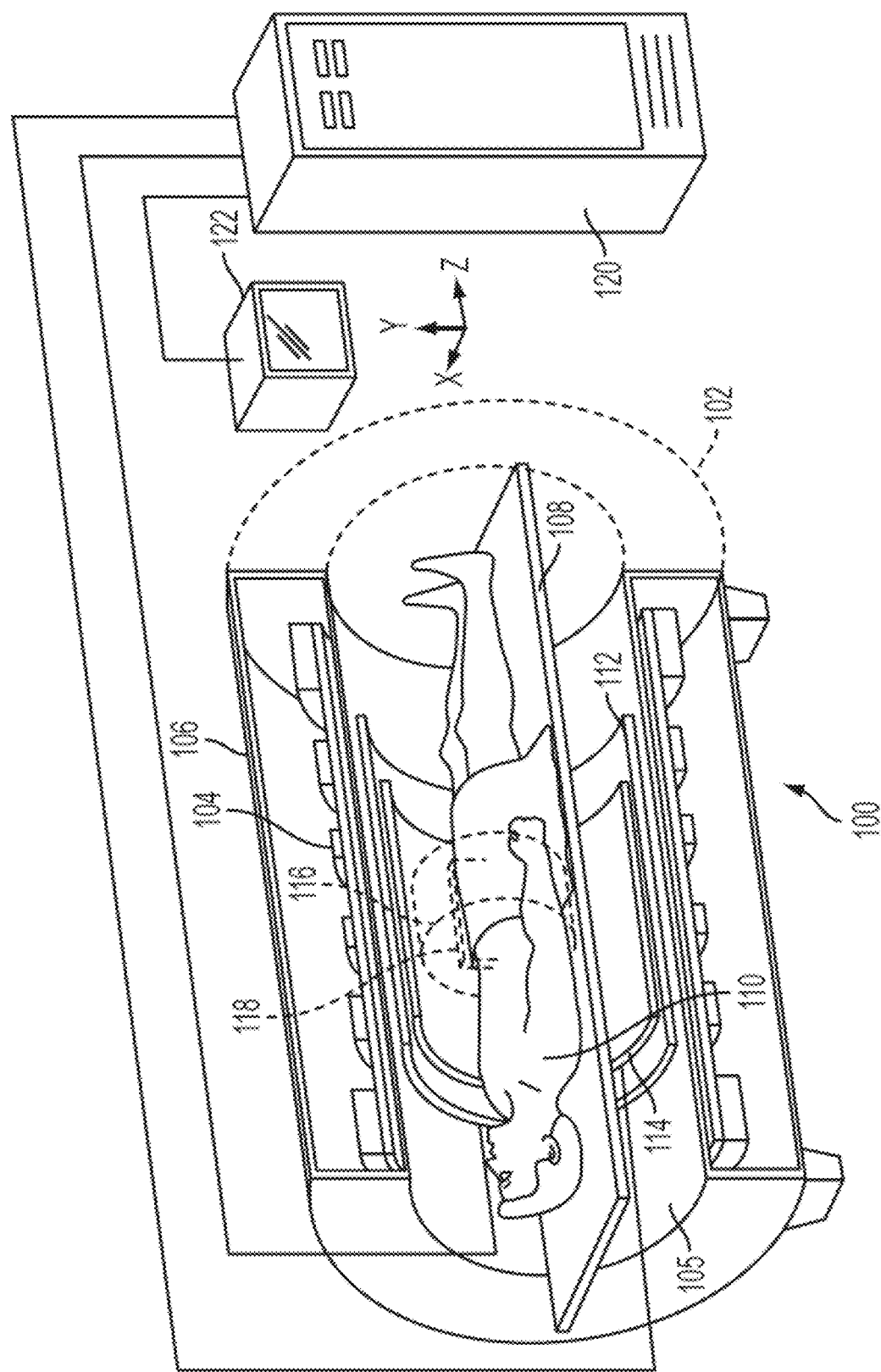
FIG. 1 depicts an exemplary MRI system in or for which the present disclosure may be implemented.

FIG. 1 shows an exemplary MRI system 100 in or for which MR imaging in accordance with examples of the present disclosure may be implemented. The illustrated MRI system 100 includes an MRI magnet assembly 102. Since the components and operation of the MRI scanner are well-known in the art, only some basic components helpful in the understanding of system 100 and its operation will be described herein.

The MRI magnet assembly 102 may include a cylindrical superconducting magnet 104 which generates a static magnetic field within a bore 105 of the superconducting magnet 104. The superconducting magnet 104 generates a substantially homogeneous magnetic field within an imaging region 116 inside the magnet bore 105. The superconducting magnet 104 may be enclosed in a magnet housing 106. A support table 108, upon which a patient 110 lies, may be disposed within the magnet bore 105. A region of interest 118 within the patient 110 may be identified and positioned within the imaging region 116 of the MRI magnet assembly 102.

A set of cylindrical magnetic field gradient coils 112 may also be provided within the magnet bore 105. The gradient coils 112 may also surround the patient 110 (or may surround the part of the patient's body of interest, such as the patient's hand and fingers). The gradient coils 112 may generate magnetic field gradients of predetermined magnitudes, at predetermined times, and in three mutually orthogonal directions within the magnet bore 105. With the magnetic field gradients, different spatial locations can be associated with different precession frequencies, thereby giving an MR image its spatial resolution. An RF transmitter coil 114 surrounds the imaging region 116 and the region of interest 118. The RF transmitter coil 114 emits RF energy in the form of a rotating magnetic field into the imaging region 116, including into the region of interest 118.

The RF transmitter coil 114 may also receive MR response signals emitted from the region of interest 118. The MR response signals may be amplified, conditioned and digitized into raw data using an image processing system 120, as is known by those of ordinary skill in the art. The image processing system 120 may further process the raw data using known computational methods, including fast Fourier transform (FFT), into an array of image data. The image data may then be displayed on a monitor 122, such as a computer CRT display, LCD display, or other suitable display.

Figure 2:
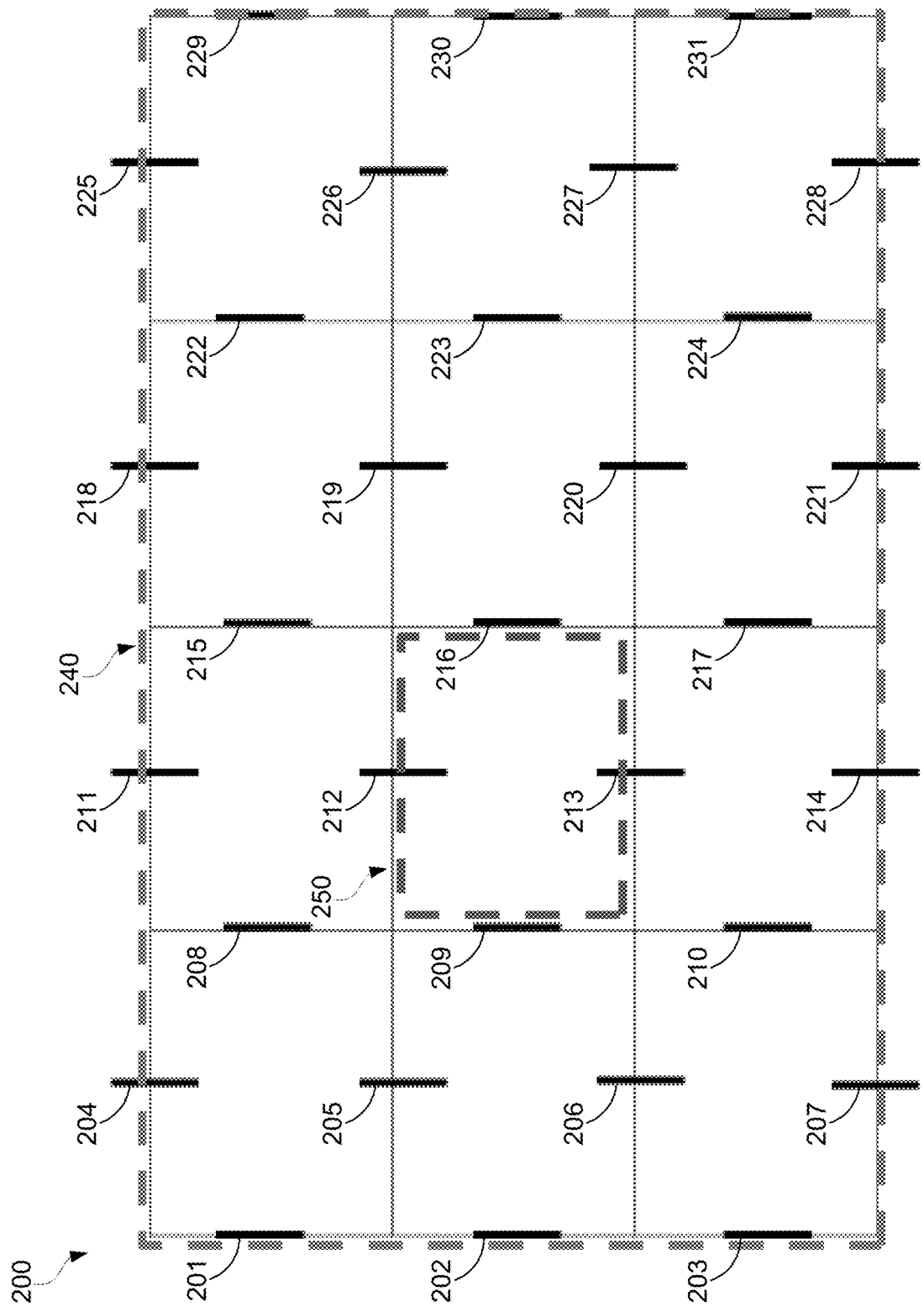
FIG. 2 depicts an example grid coil.

In some examples, the RF transmitter coil 114 may include one or more grid coils, such as grid coil 200 depicted in FIG. 2. Grid coil 200 depicts an example 31-channel MRI grid coil design. FIG. 2 depicts a 31 channel grid coil 200 design showing example positions of each transformer and integrated balun coil, the positions identified as 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, and 231. FIG. 2 also depicts two dashed boxes that represent the size and shape of the large loop coil 240 and small loop coil 250 that were built to compare the performance of the grid coil 200, which will be discussed herein.

A rectangular grid in accordance with the grid coil 200 design may be constructed of wire elements 300 including a transformer loop using wire such as 12 AWG coated copper, for example. The wire elements 300 may be twisted or otherwise formed in a loop configuration such as configurations 360, 365 depicted in FIG. 3. The wire elements 300 may each include leg segments and a loop segment. For example, wire element 300 having configuration 360 may be formed so as to have two leg segments 310, 315 and a loop segment 320. Similarly, wire element 300 having configuration 365 may be formed so as to have two leg segments 330, 335 and a loop segment 340. The wire elements 300 shown in FIG. 3 may be soldered together or otherwise fused or formed together or with other wire elements. For example, the leg segment 310 may be soldered to leg segment 330.

Figure 4:
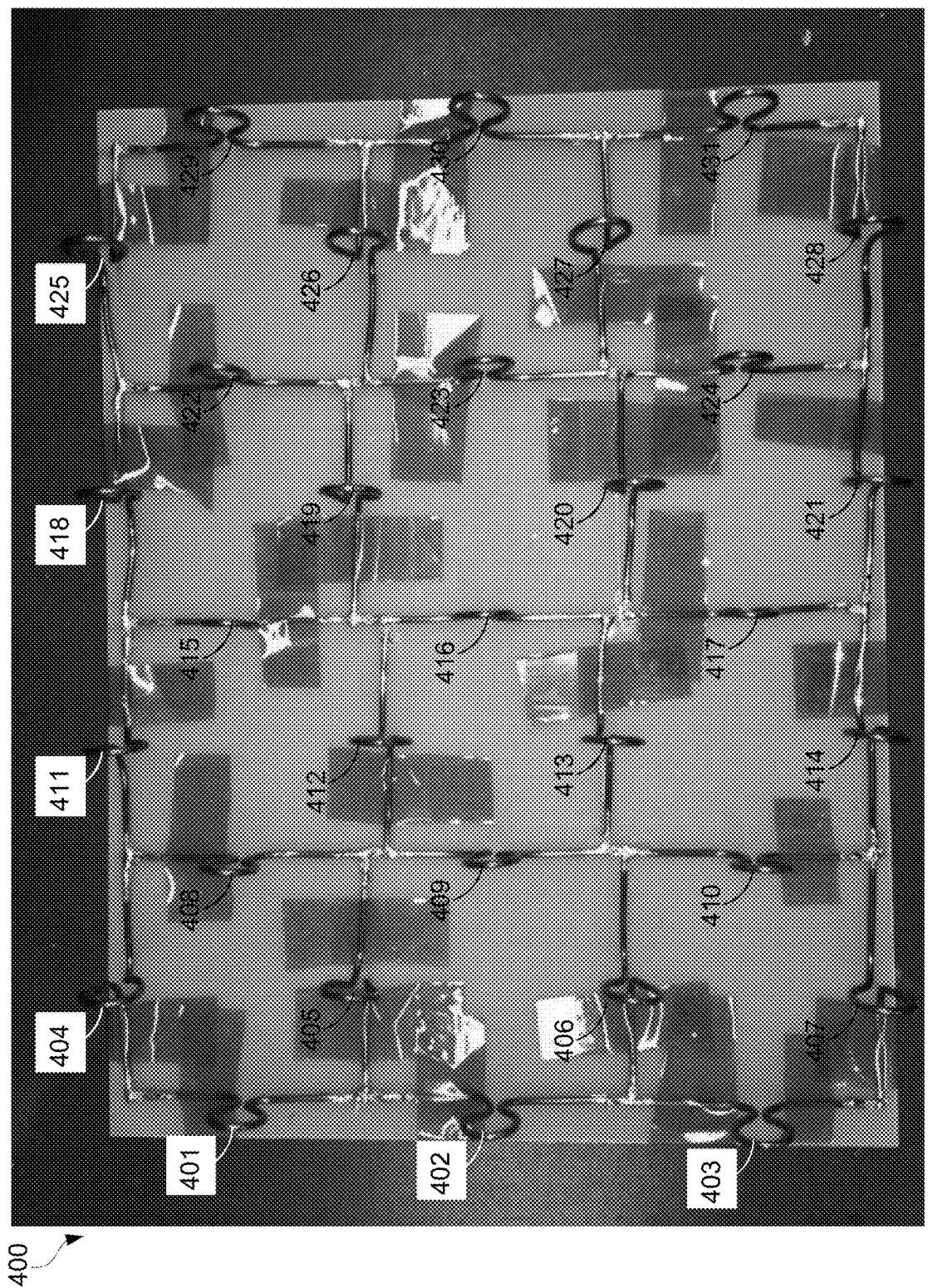
FIG. 4 depicts an example grid including example transformer elements.

An example grid 400 in which wire elements 401-431 were soldered together is depicted in FIG. 4. This example grid 400 is on a 12"×9" FR4 composite board, which includes wire elements 401-431 fastened to the FR4 composite board. Example grid 400 was constructed and tested to investigate the benefits of the grid coil 200 design. In this manner, wire elements having transformer loops were positioned at the positions identified as 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, and 431, and all of the wire elements 401-431 were soldered together. In other words, for at least a portion of the wire elements 401-431, each end of a selected wire element may be electrically attached or connected to an end of at least one other selected wire element.

It should be noted that the present disclosure is not limited to a rectilinear grid. Other configurations such as rectangular grids, triangular grids, hexagonal grids, and arbitrarily connected networks may be desirable. In particular, it may be useful to let each wire element in the grid have a unique length and orientation with respect to other wire elements in such a fashion that optimizes MR signal sensitivity for selected regions of interest. Furthermore, the grid need not be restricted to a plane. It may be advantageous to deform the grid into a cylinder, curved surface (e.g. a saddle shape), or arbitrarily shaped surface intended to closely conform to a selected region of anatomy.

The wire elements may be arranged substantially in the same plane. The plane may be warped into an arbitrary three-dimensional surface. In one example, the three-dimensional surface may be a cylinder or substantially a cylinder. In another example, the three-dimensional surface may be a portion of a cylinder or substantially a portion of a cylinder. In yet another example, the three-dimensional surface may be a portion of a saddle shape or substantially a portion of a saddle shape. The saddle shape may have both positive and negative curvature.

The wire elements may additionally or alternatively have other arrangements. In one example, the plurality of wire elements may form a rectangular grid having a substantially uniform spacing between parallel wire elements. In another example, the plurality of wire elements may form a hexagonal grid having a substantially uniform spacing between parallel wire elements. In another example, the plurality of wire elements may form a triangular grid having a substantially uniform spacing between parallel wire elements. In another example, the plurality of wire elements may form a pseudo-random grid wherein each wire element has a selected length and angular orientation that is potentially different to other wire elements. The pseudo-random grid may be configured to optimally detect MR signals from an object having a selected size and geometry.

A signal detection mechanism may rely on inductive coupling between a selected one of the wire elements and a selected one of the detector elements. However, it should be noted that the present disclosure is not limited to inductive coupling between the wire elements and the MRI system. Other coupling mechanisms such as capacitive and optical coupling may be advantageous. In particular, it may be advantageous to place a preamplifier directly on each wire element and connect the output of each preamplifier to the MRI system via a coaxial cable. Likewise, it may be advantageous to place both a preamplifier and Analog to Digital Converter (ADC) on each wire element to permit an optical connection between each wire element and the MRI system.

A substantial benefit of the present disclosure is the ability to assign unique weights to the MR signals detected by each wire element. These weights can be pre-calculated for each location within the imaging volume of the MRI system. This allows each pixel in the image to be reconstructed with a unique set of wire element weights, which in effect permits MR imaging using virtual coils. These virtual coils can represent coils which cannot be physically constructed and/or placed. For example, it is possible to create a virtual coil that would be inside the patient's body if it were physically constructed. Another advantageous aspect of the present disclosure is that the weights assigned to each wire element can provide quadrature sensitivity for every point in the imaging volume. This provides a signal to noise ratio advantage over traditional loop MR coil arrays which have limited or no sensitivity to quadrature MR signals. The MRI apparatus may use a selected mathematical weight for MR signals acquired from each wire element. The weight may be computed for each voxel in a final magnetic resonance image.

Figure 5:
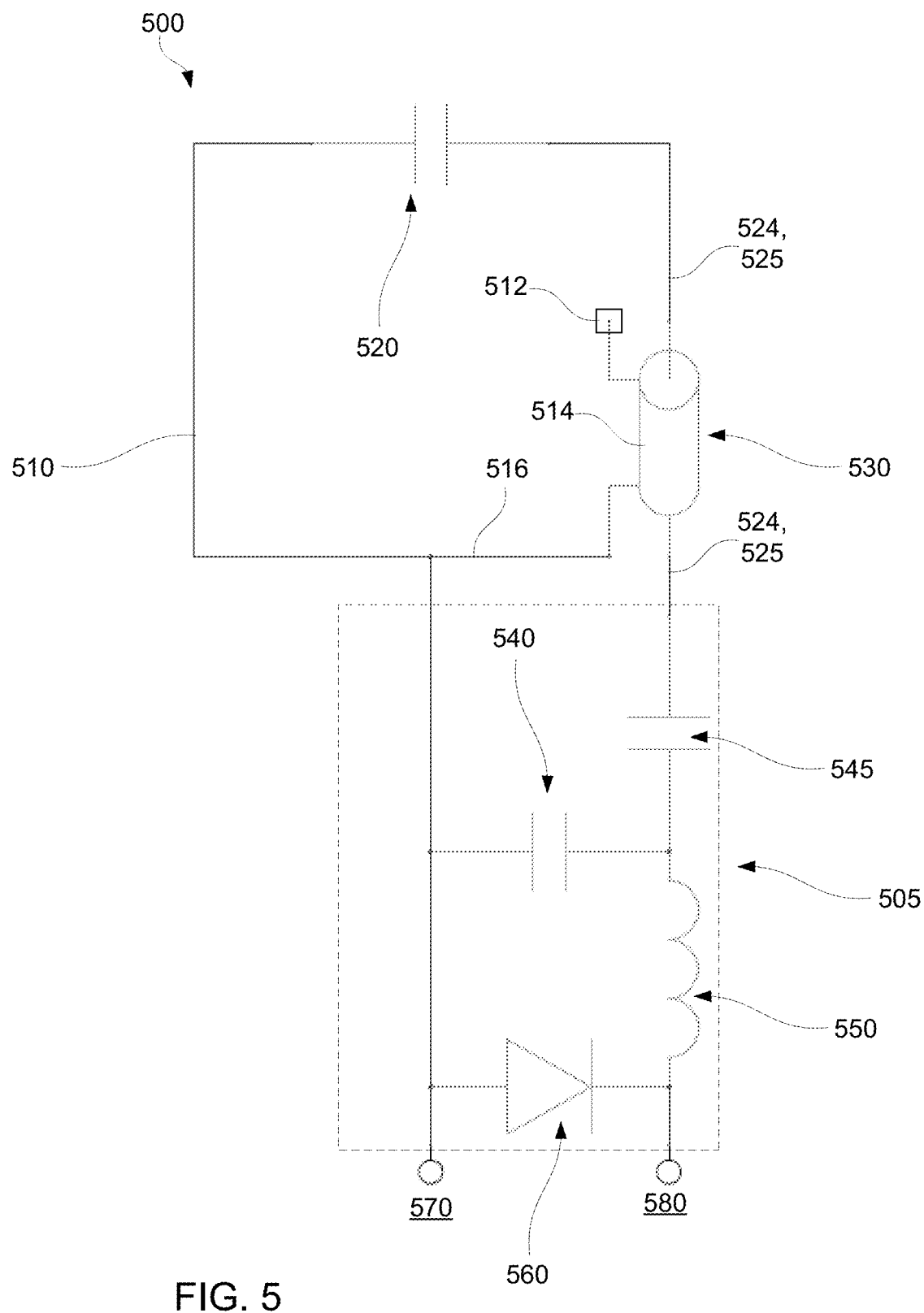
FIG. 5 is a schematic representation of an example integrated balun pickup coil.
Figure 6:
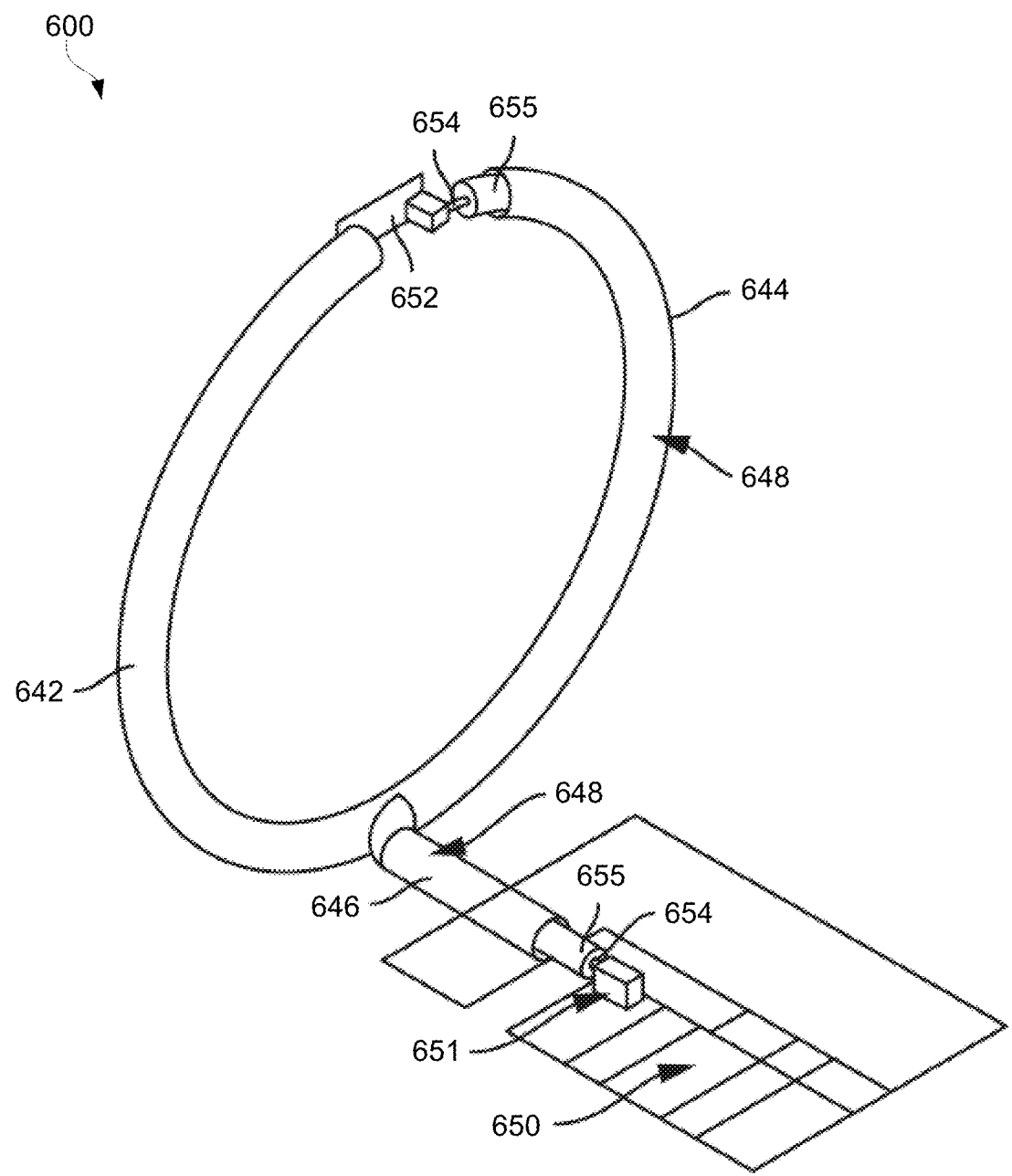
FIG. 6 depicts an example integrated balun pickup coil.

Integrated balun coils 500, 600 may be coupled to the wire elements via fasteners (e.g., nylon nuts, bolts, and washers). A circuit schematic of an example integrated balun coil 500 is shown in FIG. 5. FIG. 6 depicts an example integrated balun coil 600 arranged in accordance with the circuit schematic of FIG. 5. More details regarding the design of example integrated balun coils may be found in U.S. patent application Ser. No. 14/627,680, filed Feb. 20, 2015; the disclosure of which is incorporated herein by reference.

Integrated balun coil 500 may include a first copper tube segment 514 (or wire, trace or other sort of conductor segment) and a second copper tube 510 (or wire, trace or other sort of conductor) mounted to a matching network circuit 505. The bottom sections of the first and second copper tube segments 514, 510 are connected to a copper tube stem segment 516 extending generally axially (generally perpendicularly) from the first and second copper tube segments 514, 510 and is mounted to the matching network circuit 505 board such that the circuit board also extends generally perpendicularly from the loop coil 500. An inner conductor 524 and a dielectric insulator 525 extend through the copper tube segments 514, 516 forming a coaxial cable 530 in such segments 514, 516, where the dielectric insulator 525 separates the inner conductor 524 from the interior of the copper tube segments 514, 516. The coaxial cable 530 extends from the matching network circuit board 595 through the stem segment 516 and up through the first copper tube segment 514. At the top of the copper tube segments 514, 510 a tuning capacitor 520 is electrically coupled between the second copper tube segment 510 to the inner conductor 524 of the coaxial cable 530. The inner conductor 524 of the coaxial cable 530 is also coupled to the matching network 505 provided on the circuit board.

As depicted in this diagram, the inner conductor 524 of the coaxial cable 530 is coupled between the matching circuit 505 and the tuning capacitor 520. On the other hand, the outer conductor (the copper tube material of the first segment 514 and the stem segment 516) of the coaxial cable 530 is coupled to the matching circuit 505 at the stem segment 516 end and is unconnected (open 512) at the other end.

The matching network 505 may include a pair of matching capacitors 540, 545 and a matching inductor 550. The matching network 505 can be realized as impedance controlled microstrip line, capacitors or inductors, impedance controlled coaxial transmission lines, or a combination of them as will be apparent to those of ordinary skill. The circuit may also include a PIN diode 560 coupled between the first and second circuit leads 570, 580.

FIG. 6 depicts an example integrated balun coil 600 arranged in accordance with the circuit schematic of FIG. 5. As shown in FIG. 6, an exemplary embodiment of a loop coil 600 according to the present disclosure includes a pair of segments: a first arcuate copper tube segment 644 and a second arcuate copper tube segment 642 facing each other to form a partially enclosed loop. The bottom sections of the first and second copper tube segments 642 and 644 are connected to a copper tube stem segment 646 extending generally axially (generally perpendicularly) from the first and second copper tube segments 644, 642 and is mounted to the matching network circuit board 650 such that the circuit board 650 also extends generally perpendicularly from the loop coil 600. An inner conductor 654 and a dielectric insulator 655 extend through the copper tube segments 644 and 646 forming a coaxial cable 648 in such segments 644, 646, where the dielectric insulator 655 separates the inner conductor 654 from the interior of the copper tube segments 644 and 646. The coaxial cable 648 extends from the matching network circuit board 650 through the stem segment 646 and up through the first copper tube segment 644. At the top of the copper tube segments 642 and 644 a tuning capacitor 652 is electrically coupled between the second copper tube segment 642 to the inner conductor 654 of the coaxial cable 648. The inner conductor 654 of the coaxial cable 648 is also coupled to the matching network 651 provided on the circuit board 650.

Figure 7:
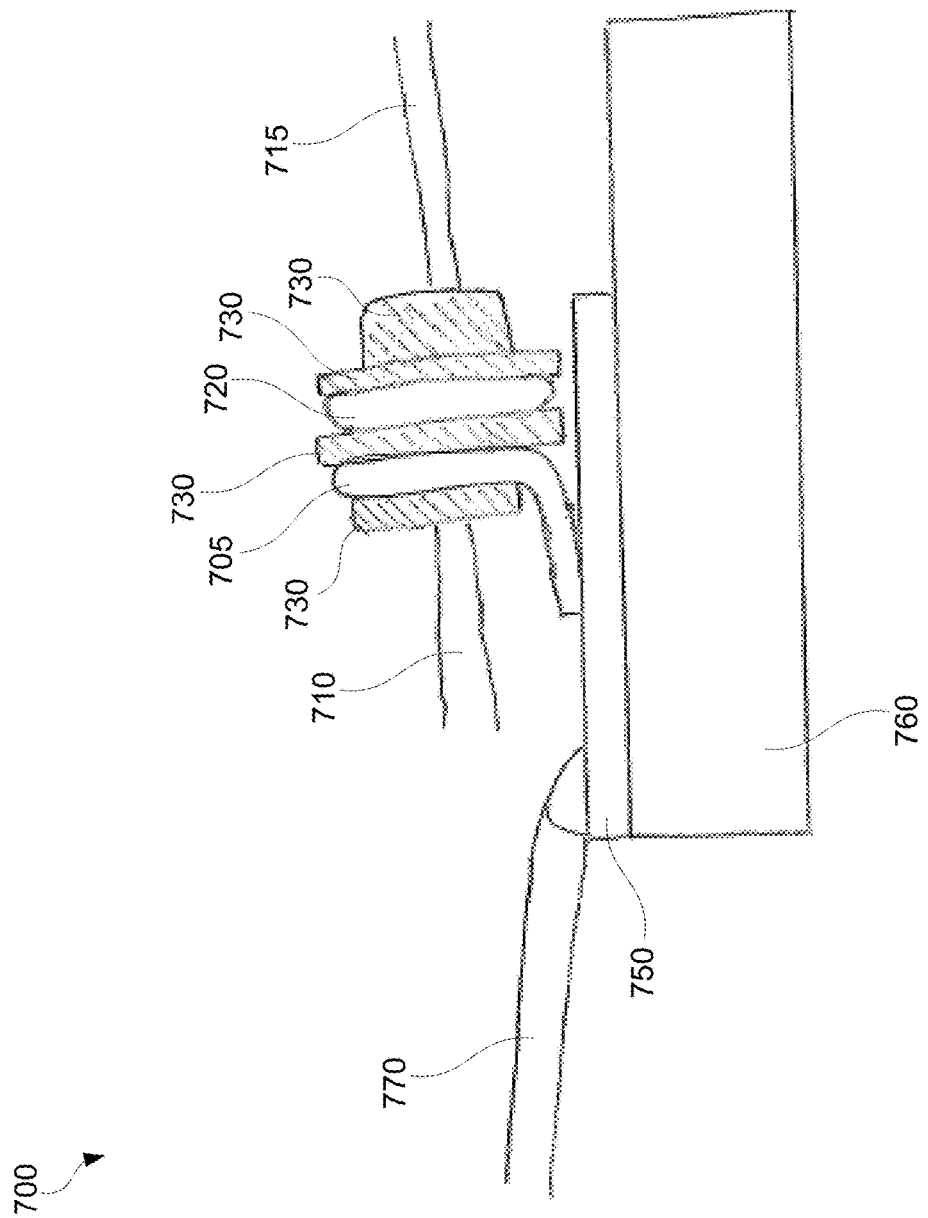
FIG. 7 depicts an example integrated balun pickup coil and example grid coil.
Figure 8:
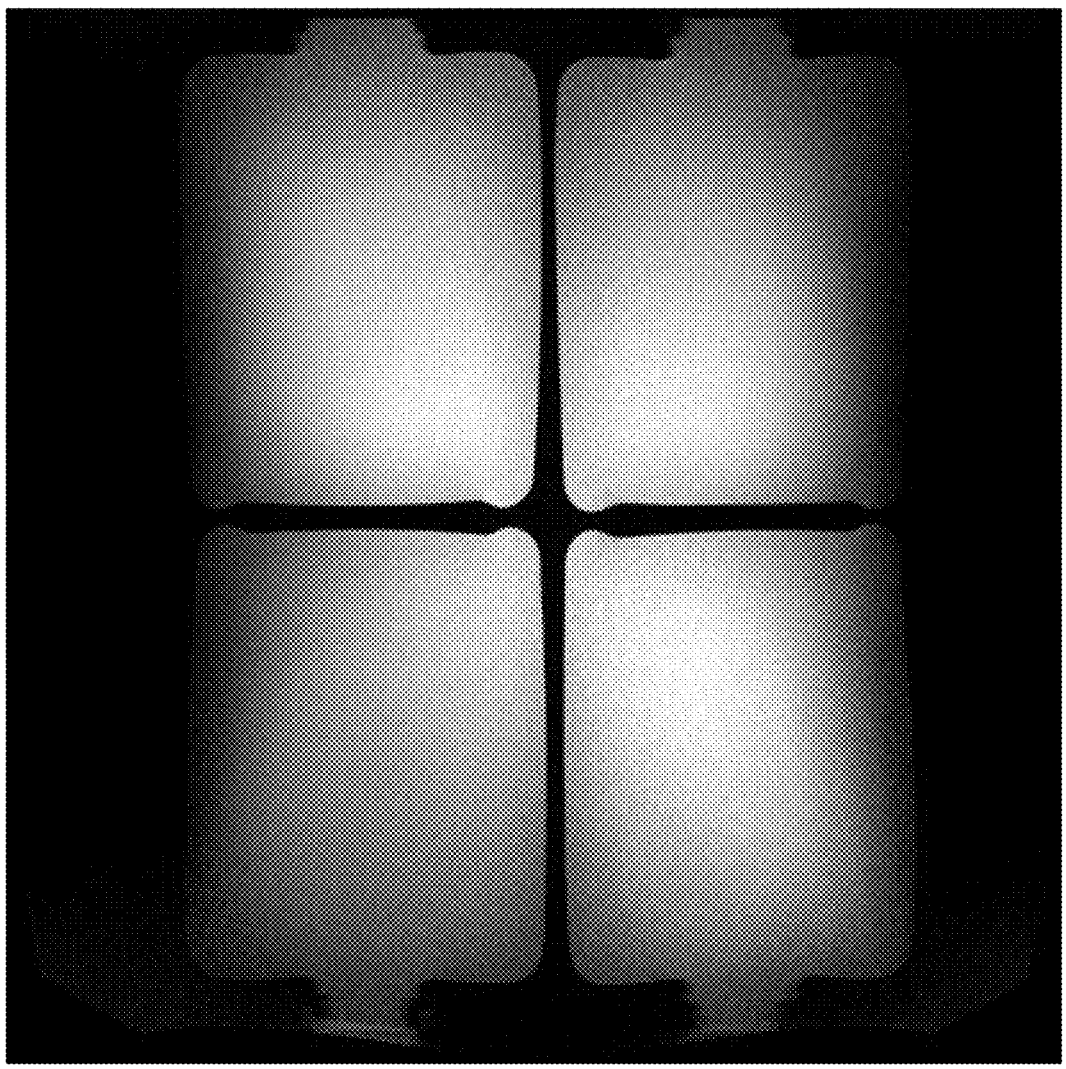
FIGS. 8-11 depict observations between example grid elements; each arranged in accordance with at least some of the embodiments disclosed in the present disclosure.
Figure 9:
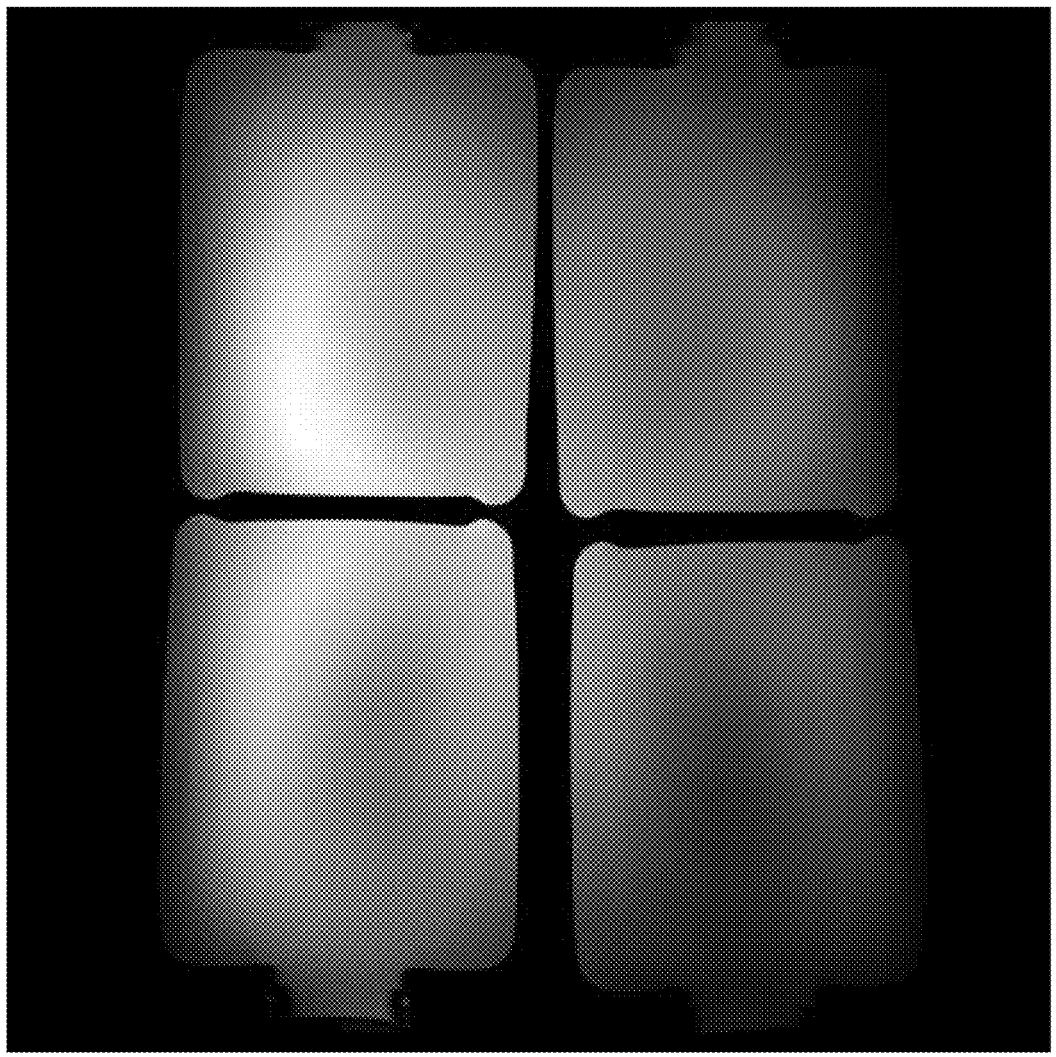
Figure 9:
Figure 10:
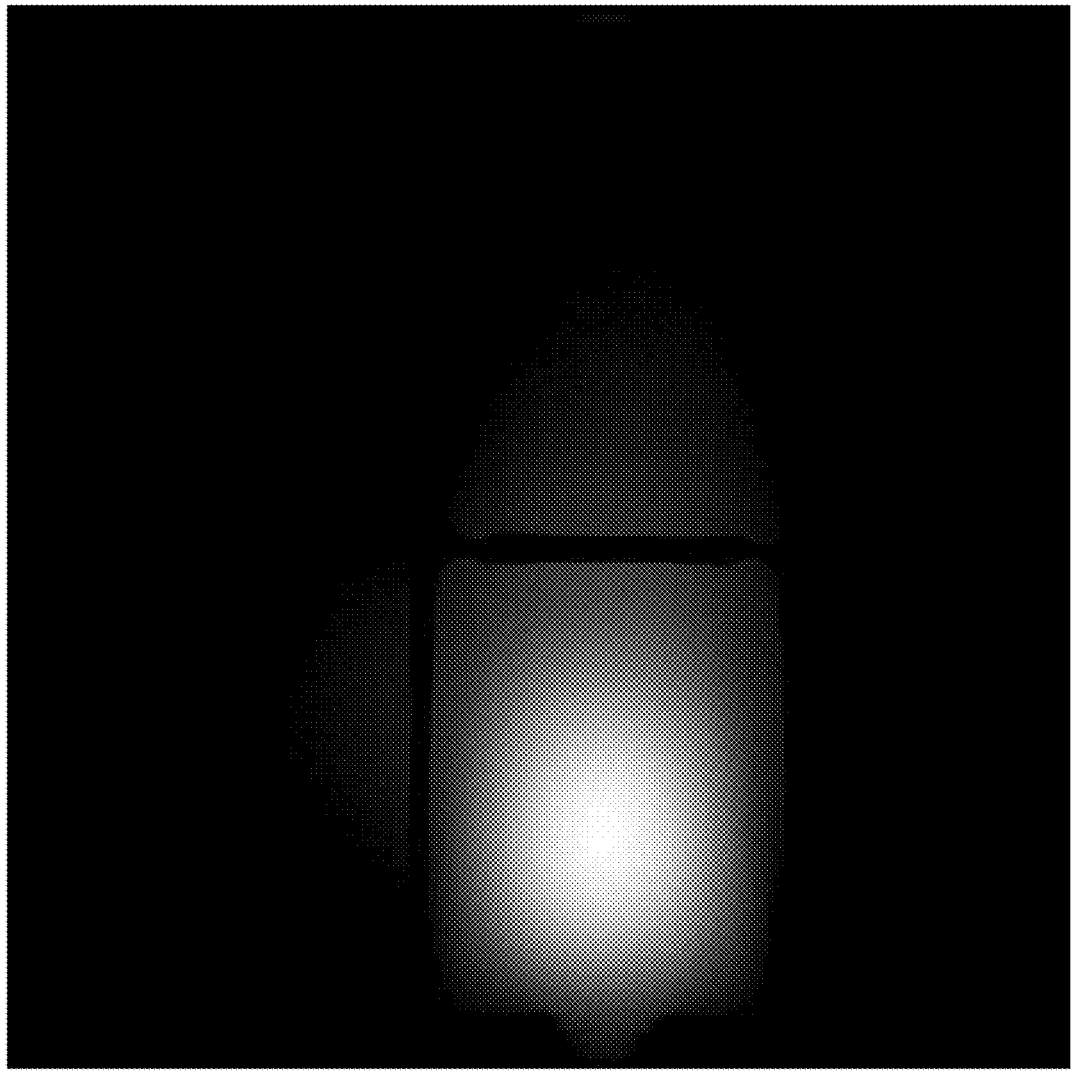
Figure 11:
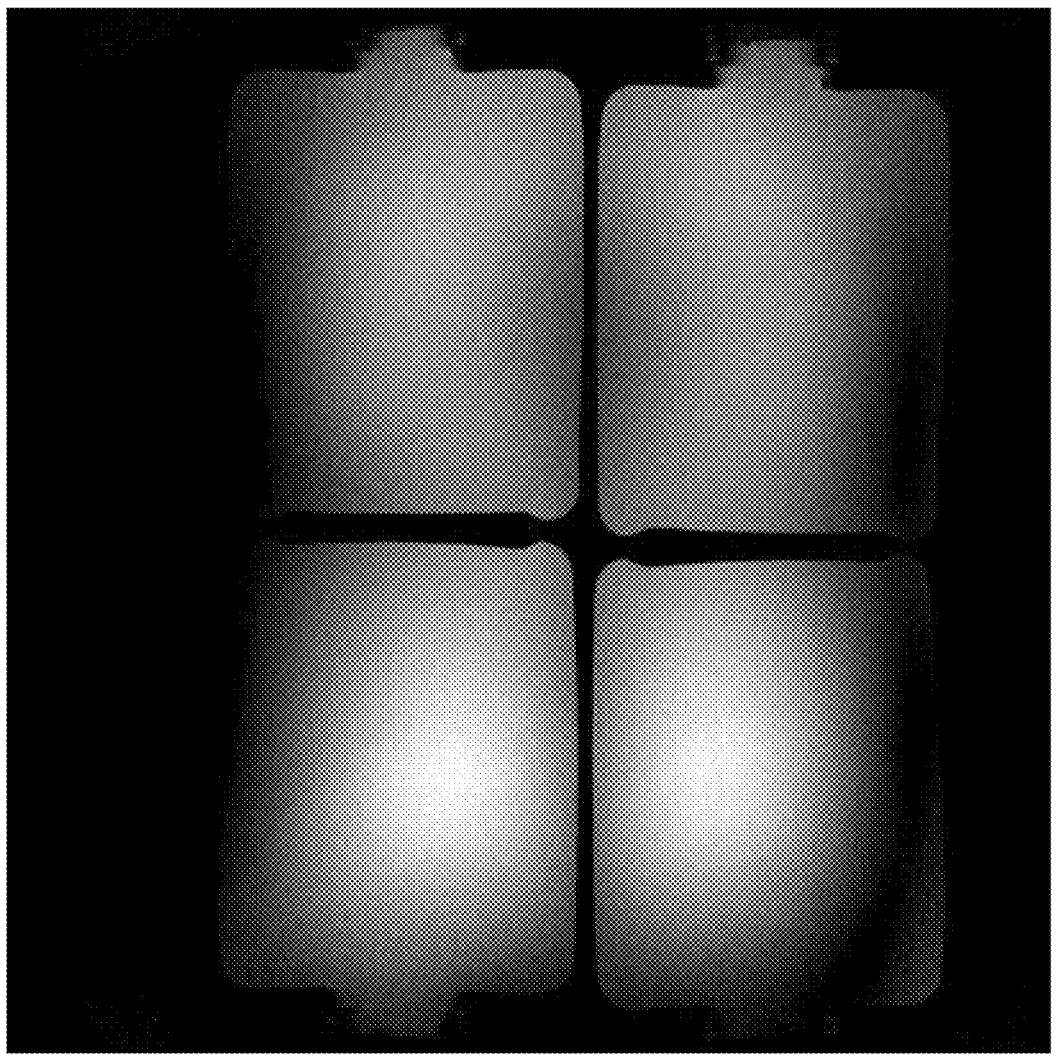

FIG. 7 depicts an example assembly 700 coupling an integrated balun coil assembly to a grid coil wire element having leg segments 710, 715 and a loop segment 720. The integrated balun coil assembly in this example includes an integrated balun coil loop 705, a circuit board 750, and a non-conductive base 760 for the integrated balun coil assembly. may be a Lexan block or other non-conductive materials.

Integrated balun coil loop 705 may be coupled to each grid coil loop 720 on the grid using a non-conductive alignment cradle 730. In some examples, the non-conductive alignment cradle 730 may include nylon nuts, nylon bolts, and/or nylon washers. Other non-conductive materials may also be used to construct the non-conductive alignment cradle 730. The non-conductive alignment cradle 730 secures the integrated balun coil loop 705 and the loop segment 720 of a grid coil coaxially across from each other. The non-conductive alignment cradle 730 also maintains positions of the integrated balun coil loop 705 and the loop segment 720 of a grid coil relative to each other. The non-conductive base 760 for the integrated balun coil assembly may be a Lexan block or other non-conductive material.

Figure 3:
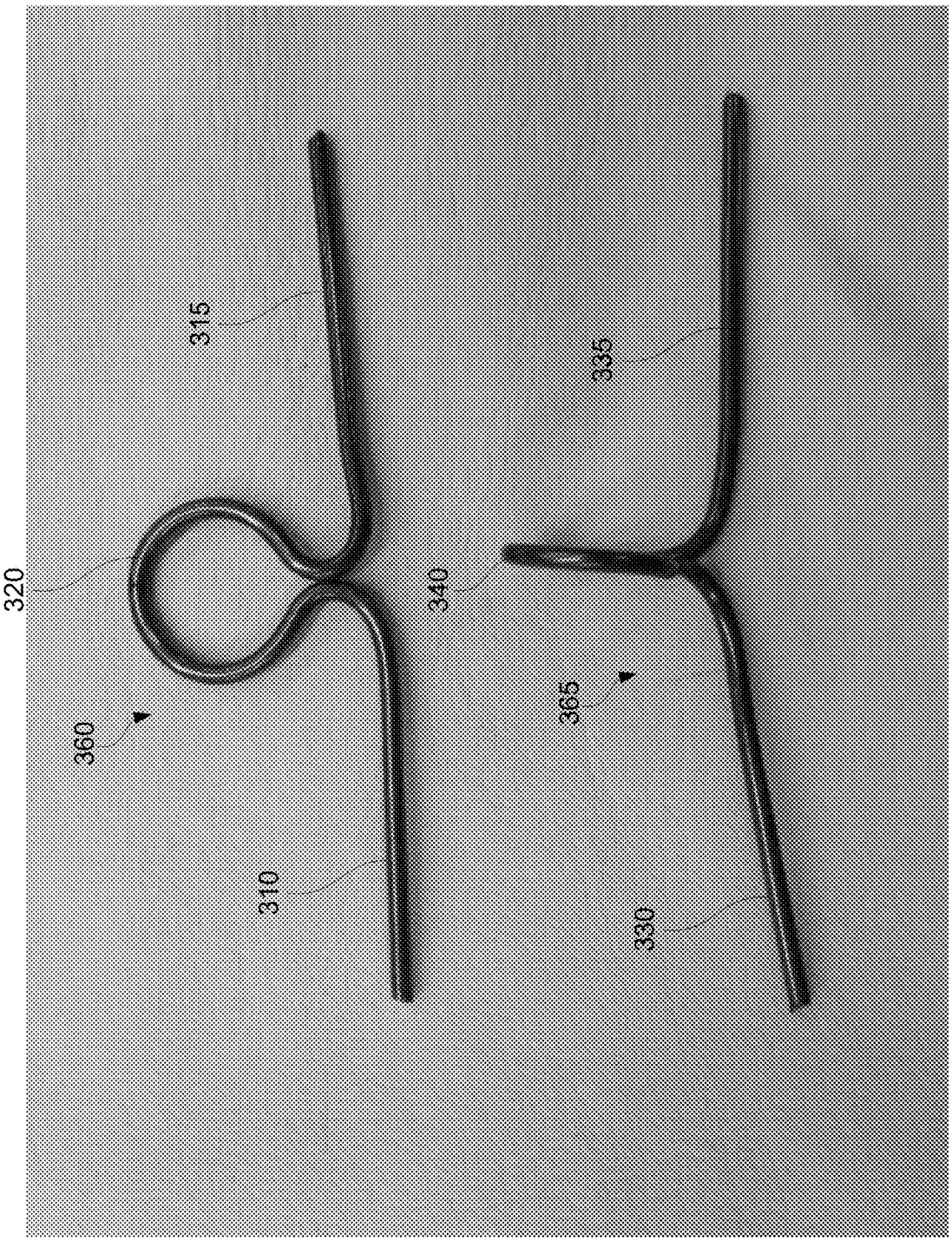
FIG. 3 depicts example transformer elements.

An example 31 channel grid coil with integrated balun coil configuration was constructed in accordance with the configuration shown in FIG. 4. The dimensions of the squares were chosen to be 70 mm×70 mm after empirically determining the distances required for −30 dB coupling between pickup coils. Each of the 31 transformer elements were individually cut and bent out of 12 gauge coated copper wire as depicted in FIG. 3. They were then soldered into a 3×4 rectangular grid and mounted on a FR4 12×9 inch board. Twenty-eight 300 pF capacitors were soldered at selected joints to interrupt eddy currents. The grid was modified from the symmetric square pattern to a rectangular pattern to minimize use of capacitors, measuring 220 mm×285 mm in total.

Example integrated balun coils were constructed using 2.196 mm diameter semi-rigid coaxial cable. The diameter of the coils matched the diameter of the transformer elements on the grid for optimal inductive coupling. Each example pickup coil is composed of a segment of the copper coaxial cable, a small feeder board, multiple capacitors for tuning, and a diode and an inductor for detuning during transmit. Each pickup coil was individually tuned to 127.74 MHz, the Larmor frequency of protons at 3 T.

MR images 800 were taken with the example 31 channel grid coil on a Philips Achieva 3 Tesla MRI system and were compared to images 900, 1000, 1100 taken with a size-matched large loop coil 240 (see images 1100), a small loop coil 250 (see images 1000), and a commercially-made 16 channel array (see images 900). These images are shown in FIGS. 8-11.

Network measurements were performed with a Rhode & Schwarz ZNC 3 Network Analyzer. The coupling of the transformer to the pickup coil was found to be −3.2 dB. Isolation between individual grid elements was also measured and found to be better than typically found in conventional phased array coils.

A large rectangular traditional coil (the size of box 240) measuring 215 mm×295 mm and a small square traditional coil (the size of box 250) measuring 75 mm×75 mm were constructed. Images were acquired with the example 31 channel grid coil and the two traditional coils 240, 250 to compare their sensitivity profile and SNR.

MR images 800, 900, 1000, 1100 were acquired with a Philips 3 T Achieva (Philips Healthcare, Best, Netherlands) MRI system. For phantom imaging, a T2 weighted turbo spin echo sequence was used with a 90° flip angle, TR=300 msec, a TE=4.5 msec, an FOV of 400 mm×400 mm, and a slice thickness of 4 mm. Four 2-liter bottles were used as phantoms, each containing a solution of 2 g/l $NaCl_2$ and 1 g/l $CuSO_4$. These phantoms provided a large homogenous medium for the evaluation of sensitivity profile of the imaging coils.

In this example, the highest inter-channel coupling was observed at the positions between adjacent grid element positions 411 and 412. This coupling was observed to be −13.3 dB. 94.6% of coil couplings had better than −20 dB isolation.

Signal to noise measurements were taken both close to the coil where the signal was at its highest intensity and in the center of the phantoms. Close to the surface of the phantom the grid coil (depicted in FIG. 8) had the highest SNR followed by the small loop (depicted in FIG. 10), large loop (depicted in FIG. 11), and 16 channel commercial phased array (depicted in FIG. 9) with signal-to-noise ratios of 36.08, 35.35, 14.48, and 7.54 respectively. In the center of the phantoms, the grid coil had the second highest SNR (12.48) with the small loop having an SNR of 20.67

In these examples, the grid coil had better SNR than the two traditional coils 240, 250 tested and required fewer parts to construct than the commercial phased array. Furthermore, the grid coil showed better isolation between channels than the traditional phased array. This feature alone may provide enhanced image performance for high acceleration factors. Further, the grid approach may use current measurements from individual grid elements to synthesize other coils, including coils that cannot be physically constructed. (e.g. a hypothetical surface coil disposed inside the body with its corresponding SNR advantage for small regions of interest such as a single chamber of the heart). The grid approach may be further optimized, and new grid layouts may include other shapes and/or configurations, including offset squares, hexagons, and octagons, for example. This may maximize or improve SNR, image acceleration factors, and/or image uniformity.

Some examples of the present disclosure may eliminate the need for specialized surface coils. In some examples,

- Synthetic coils may be created with a single grid. This may eliminate the need for specifically designed surface coils.
- The grid does not load to the body. This may make the coil easier to construct.
- High acceleration factors are likely due to the increased isolation between imaging channels.
- The grid approach improves SNR with multiple channels while maintaining a large FOV.
- Every pickup coil in the grid may be identical. This may improve manufacturability and robustness.

While the foregoing disclosure includes many details and specificities, it is to be understood that these have been included for purposes of explanation and example only, and are not to be interpreted as limitations of the present disclosure. It will be apparent to those skilled in the art that other modifications to the embodiments described above can be made without departing from the spirit and scope of the present disclosure. Accordingly, such modifications are to be considered within the scope of the present disclosure.

Likewise, it is to be understood that it is not necessary to meet any or all of the identified advantages or objects of the present disclosure in order to fall within the scope of the present disclosure, since inherent and/or unforeseen advantages of such inventions may exist even though they may not have been explicitly discussed herein.

All publications, articles, patents and patent applications cited herein are incorporated into the present disclosure by reference to the same extent as if each individual publication, article, patent application, or patent was specifically and individually indicated to be incorporated by reference.

What is claimed is:

1. A magnetic resonance (MR) signal detector grid assembly adapted for detection of signals in a magnetic resonance imaging (MRI) apparatus, comprising:
   a non-resonant grid of a plurality of wire elements, wherein at least one end of a selected wire element is electrically attached to an end of at least one other selected wire element; and
   a plurality of detector elements, each detector element being configured to detect an MR signal induced on a given one of the wire elements in the non-resonant grid.

2. The MR signal detector grid assembly of claim 1, wherein the plurality of wire elements are substantially in the same plane.

3. The MR signal detector grid assembly of claim 2, wherein the plane is warped into an arbitrary three-dimensional surface.

4. The MR signal detector grid assembly of claim 3, wherein the three-dimensional surface is substantially a cylinder.

5. The MR signal detector grid assembly of claim 3, wherein the three-dimensional surface is substantially a portion of a cylinder.

6. The MR signal detector grid assembly of claim 3, wherein the three-dimensional surface is substantially a portion of a saddle shape.

7. The MR signal detector grid assembly of claim 1, wherein the plurality of wire elements form a rectilinear grid having a substantially uniform spacing between parallel wire elements.

8. The MR signal detector grid assembly of claim 1, wherein the plurality of wire elements form a hexagonal grid having a substantially uniform spacing between parallel wire elements.

9. The MR signal detector grid assembly of claim 1, wherein the plurality of wire elements form a triangular grid having a substantially uniform spacing between parallel wire elements.

10. The MR signal detector grid assembly of claim 1, wherein the plurality of wire elements form pseudo-random grid.

11. The MR signal detector grid assembly of claim 10, wherein each wire element has a selected length and angular orientation that is different than at least one of the other wire elements.

12. The MR signal detector grid assembly of claim 10, wherein the pseudo-random grid is configured to optimally detect MR signals from an object having a selected size and geometry.

13. The MR signal detector grid assembly of claim 1, wherein said signal detection relies on inductive coupling between a selected one of the wire elements and a selected one of the detector elements.

14. The MR signal detector grid assembly of claim 1, wherein said signal detection relies on capacitive coupling between a selected one of the wire elements and a selected one of the detector elements.

15. The MR signal detector grid assembly of claim 1, further comprising a preamplifier connected to a selected one of the wire elements.

16. The MR signal detector grid assembly of claim 1, wherein one or more detected MR signals are transmitted to the MRI apparatus via a coaxial cable.

17. The MR signal detector grid assembly of claim 1, wherein said MRI apparatus uses a selected mathematical weight for MR signals acquired from each wire element, said weight being computed for each voxel in a final magnetic resonance image.

* * * * *